(12) United States Patent  
Heruth et al.

(10) Patent No.: US 7,930,037 B2
(45) Date of Patent: Apr. 19, 2011

(54) FIELD STEERABLE ELECTRICAL STIMULATION PADDLE, LEAD SYSTEM, AND MEDICAL DEVICE INCORPORATING THE SAME

(75) Inventors: Kenneth T. Heruth, Edina, MN (US); Mark Holle, Shoreview, MN (US); James Skakoon, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/846,329

(22) Filed: May 14, 2004

(65) Prior Publication Data

US 2005/0070982 A1   Mar. 31, 2005

Related U.S. Application Data

(60) Provisional application No. 60/507,832, filed on Oct. 1, 2003, provisional application No. 60/507,389, filed on Sep. 30, 2003.

(51) Int. Cl.
 *A61N 1/05* (2006.01)
(52) U.S. Cl. .................................. 607/116; 607/117
(58) Field of Classification Search .............. 607/46, 607/43, 118, 115–117; 600/377
See application file for complete search history.

(56) References Cited

U.S. PATENT DOCUMENTS

| 5,117,826 | A |   | 6/1992  | Bartelt et al. |
|---|---|---|---|---|
| 5,370,665 | A |   | 12/1994 | Hudrlik |
| 5,476,485 | A | * | 12/1995 | Weinberg et al. ............. 607/28 |
| 5,496,369 | A |   | 3/1996  | Howard, III |
| 5,501,703 | A |   | 3/1996  | Holsheimer et al. |
| 5,643,330 | A |   | 7/1997  | Holsheimer et al. |
| 5,676,655 | A |   | 10/1997 | Howard, III et al. |
| 5,697,975 | A |   | 12/1997 | Howard, III et al. |
| 5,713,847 | A |   | 2/1998  | Howard, III et al. |
| 5,713,922 | A |   | 2/1998  | King |
| 5,735,885 | A |   | 4/1998  | Howard, III et al. |
| 5,800,465 | A |   | 9/1998  | Thompson et al. |
| 5,800,535 | A |   | 9/1998  | Howard, III |

(Continued)

FOREIGN PATENT DOCUMENTS

EP   0557562 A1   1/1993

(Continued)

OTHER PUBLICATIONS

Karatas, A., S. Caglar, A. Savas, A. Elhan, and A. Erdogan. "Microsurgical Anatomy of the Dorsal Cervical Rootlets and Dorsal Root Entry Zones." Acta Neurochirurgica 147.2 (2005): 195-199. Nov. 19, 2007 <http://www.springerlink.com/content/qp81d2y5npaa4ehy/>.*

(Continued)

*Primary Examiner* — Eric D. Bertram

(57) ABSTRACT

An implantable electrode paddle is adapted to receive an electrical signal from a medical device and generate an electrical field to stimulate selected body tissue. The paddle includes a housing including walls that define an interior space and a plurality of windows formed through at least a first one of the walls for transmitting the electrical field to the body tissue, an electrode array including a plurality of electrode groups, each electrode group including at least two electrodes individually secured in a respective window and spaced between about 0.1 mm and about 10 mm apart, and a plurality of wires, each of the wires being coupled to a respective electrode and routed within the interior space to receive the electrical signal. A lead assembly and an implantable medical device can include the paddle.

25 Claims, 10 Drawing Sheets

U.S. PATENT DOCUMENTS

| | | | |
|---|---|---|---|
| 5,820,588 A | 10/1998 | Howard, III | |
| 5,843,093 A | 12/1998 | Howard, III | |
| 5,895,416 A * | 4/1999 | Barreras et al. | 607/62 |
| 5,925,070 A | 7/1999 | King et al. | |
| 6,024,702 A | 2/2000 | Iversen | |
| 6,038,480 A * | 3/2000 | Hrdlicka et al. | 607/116 |
| 6,052,624 A | 4/2000 | Mann et al. | |
| 6,083,252 A | 7/2000 | King et al. | |
| 6,129,685 A | 10/2000 | Howard, III | |
| 6,263,225 B1 | 7/2001 | Howard, III | |
| 6,393,325 B1 | 5/2002 | Mann et al. | |
| 6,421,566 B1 | 7/2002 | Holsheimer | |
| 6,456,886 B1 | 9/2002 | Howard, III et al. | |
| 6,473,653 B1 * | 10/2002 | Schallhorn et al. | 607/116 |
| 6,505,078 B1 * | 1/2003 | King et al. | 607/67 |
| 6,510,347 B2 | 1/2003 | Borkan | |
| 6,516,227 B1 | 2/2003 | Meadows et al. | |
| 6,522,932 B1 * | 2/2003 | Kuzma et al. | 607/116 |
| 6,609,032 B1 | 8/2003 | Woods et al. | |
| 7,107,097 B2 * | 9/2006 | Stern et al. | 607/2 |
| 2001/0034542 A1 | 10/2001 | Mann | |
| 2002/0111661 A1 * | 8/2002 | Cross et al. | 607/117 |
| 2002/0128694 A1 | 9/2002 | Holsheimer | |
| 2002/0143376 A1 * | 10/2002 | Chinn et al. | 607/115 |
| 2003/0018370 A1 | 1/2003 | King et al. | |
| 2003/0083724 A1 | 5/2003 | Jog et al. | |
| 2003/0093130 A1 | 5/2003 | Stypulkowski | |
| 2003/0114899 A1 | 6/2003 | Woods et al. | |
| 2003/0120323 A1 | 6/2003 | Meadows et al. | |
| 2003/0187491 A1 | 10/2003 | Greenburg et al. | |
| 2003/0195582 A1 | 10/2003 | Mann | |
| 2003/0204228 A1 * | 10/2003 | Cross et al. | 607/116 |
| 2003/0236562 A1 * | 12/2003 | Kuzma | 607/122 |
| 2004/0015221 A1 * | 1/2004 | Kuzma | 607/116 |
| 2004/0034394 A1 | 2/2004 | Woods et al. | |
| 2006/0069415 A1 * | 3/2006 | Cameron et al. | 607/45 |

FOREIGN PATENT DOCUMENTS

| | | |
|---|---|---|
| WO | WO-94/17855 | 8/1994 |
| WO | WO-95/19804 | 7/1995 |
| WO | WO 9521591 | 8/1995 |
| WO | WO-97/37721 | 10/1997 |
| WO | WO-98/40120 | 9/1998 |
| WO | WO 9900067 | 1/1999 |
| WO | WO-99/49934 A1 | 10/1999 |
| WO | WO 0143818 | 6/2001 |
| WO | WO-02/092165 A1 | 11/2002 |
| WO | WO-03/041795 A1 | 5/2003 |

OTHER PUBLICATIONS

Grill et al, Stimulus Waveforms for Selective Neural Stimulation, *IEEE Engineering in Medicine and Biology*, Jul./Aug. 1995.

Grill et al, Inversion of the Current-Distance Relationship by Transient Depolarization, *IEEE Transactions on Biomedical Engineering*, Jan. 1997, vol. 44, No. 1.

International Search Report, Application No. PCT/US2004/031750, mailed Jan. 17, 2005.

* cited by examiner

FIELD STEERABLE ELECTRICAL STIMULATION PADDLE, LEAD SYSTEM, AND MEDICAL DEVICE INCORPORATING THE SAME

This application claims the benefit of U.S. Provisional Application No. 60/507,832, filed Oct. 1, 2003, and 60/507,389, filed Sep. 30, 2003 which are hereby incorporated herein by reference in their entirety.

TECHNICAL FIELD

The present invention generally relates to medical leads for biological tissue therapy, and more particularly relates to systems and methods for steering a tissue stimulating electrical field using implantable medical leads.

BACKGROUND

Dorsal columns are long myelinated fibers oriented along the spinal cord axis and centrally located around the lumbar spine between the dorsal roots. Researchers have found that fibers enter the dorsal horn, and are arranged in approximately v-shaped layers. Fibers that enter at a higher vertebral level form a v-shaped layer covering the layers that originated at lower levels. The nerve fiber organization is less structured below the dorsal column surface, where the fibers are two or more vertebral levels away from their point of entry. M. C. Smith et al., *Topographical Anatomy of the Posterior Columns of the Spinal Cord in Man*, 107 Brain 671 (1984). FIG. 1 is a cross sectional view of different vertebra through the spinal cord with symbols illustrating the spinal nerve pathways through the dorsal column.

Chronic pain originating in the lower back is quite common. Spinal cord stimulation is an accepted therapy for chronic pain. However, physicians have found that it can be difficult to properly position the spinal cord stimulation lead to achieve good pain relief for lower back pain. As illustrated in FIG. 1, nerve fibers associated with lower back pain (S4 to L5), are only close to the dorsal column surface for a short distance and are consequently difficult to locate. Physicians who consider properly treating lower back pain with SCS must develop an effective SCS technique and must learn to manipulate a stimulating lead with unusual skill and patience. Such a technique often involves implanting a stimulating device and carefully positioning at least one stimulating lead into a patient's spinal area. Even if the technique is performed properly, the leads may need to be repositioned over time. Repositioning the stimulating leads is typically an invasive surgical procedure that carries risks and requires great patience, care, and skill.

Accordingly, it is desirable to provide a system and method that physicians can readily adopt for stimulating the spinal cord, particularly areas of the spinal cord that have low surface concentrations of readily manipulated nerves such as those in the dorsal columns. In addition, it is desirable to provide a system and method for non-invasively relocating an electrical field after the system is implanted. Furthermore, other desirable features and characteristics of the present invention will become apparent from the subsequent detailed description and the appended claims, taken in conjunction with the accompanying drawings and the foregoing technical field and background.

BRIEF SUMMARY

An implantable electrode paddle is provided for receiving an electrical signal from a medical device and generating an electrical field to stimulate selected body tissue. The electrode paddle comprises a housing including walls that define an interior space and a plurality of windows formed through at least a first one of the walls for transmitting the electrical field to the body tissue, an electrode array including a plurality of electrode groups, each electrode group including at least two electrodes individually secured in a respective window and spaced between about 0.1 mm and about 10 mm apart, and a plurality of wires, each of the wires being coupled to a respective electrode and routed within the interior space to receive the electrical signal.

An implantable lead system is provided to transmit an electrical signal from a medical device and generate an electrical field to stimulate selected body tissue. The system comprises a first lead body comprising at least one conductor, and the electrode paddle described above.

An implantable medical device is also provided for generating an electrical field to stimulate selected body tissue. The device comprises a controlling device such as an electrical pulse generator having an electrical output for transmitting electrical signals, and the lead body and electrode paddle described above.

A method is provided for manufacturing an implantable electrode paddle that is adapted to receive an electrical signal from a medical device and generate an electrical field to stimulate selected body tissue. The method comprises the step of assembling an electrode array including a plurality of electrode groups, and a plurality of wires coupled to the electrode array, onto a first insulative substrate having a plurality of windows formed therethrough for transmitting the electrical field to the body tissue, and securing each electrode in a respective window with the electrodes in each group spaced between about 0.1 mm and about 10 mm apart.

BRIEF DESCRIPTION OF THE DRAWINGS

The present invention will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 1:
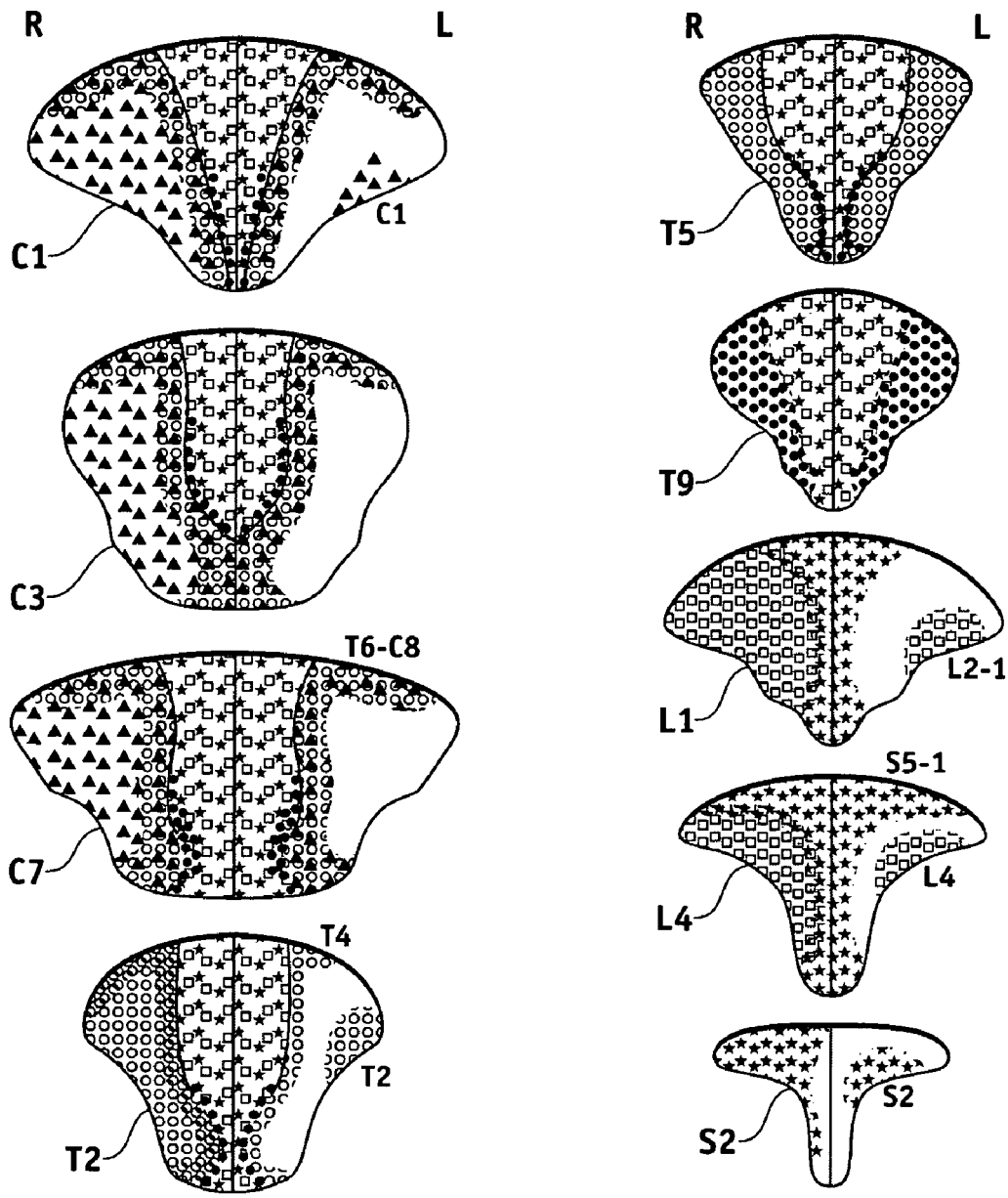
FIG. 1 is a cross sectional view of different vertebra through the spinal cord with symbols illustrating the spinal nerve pathways through the dorsal column.
Figure 2:
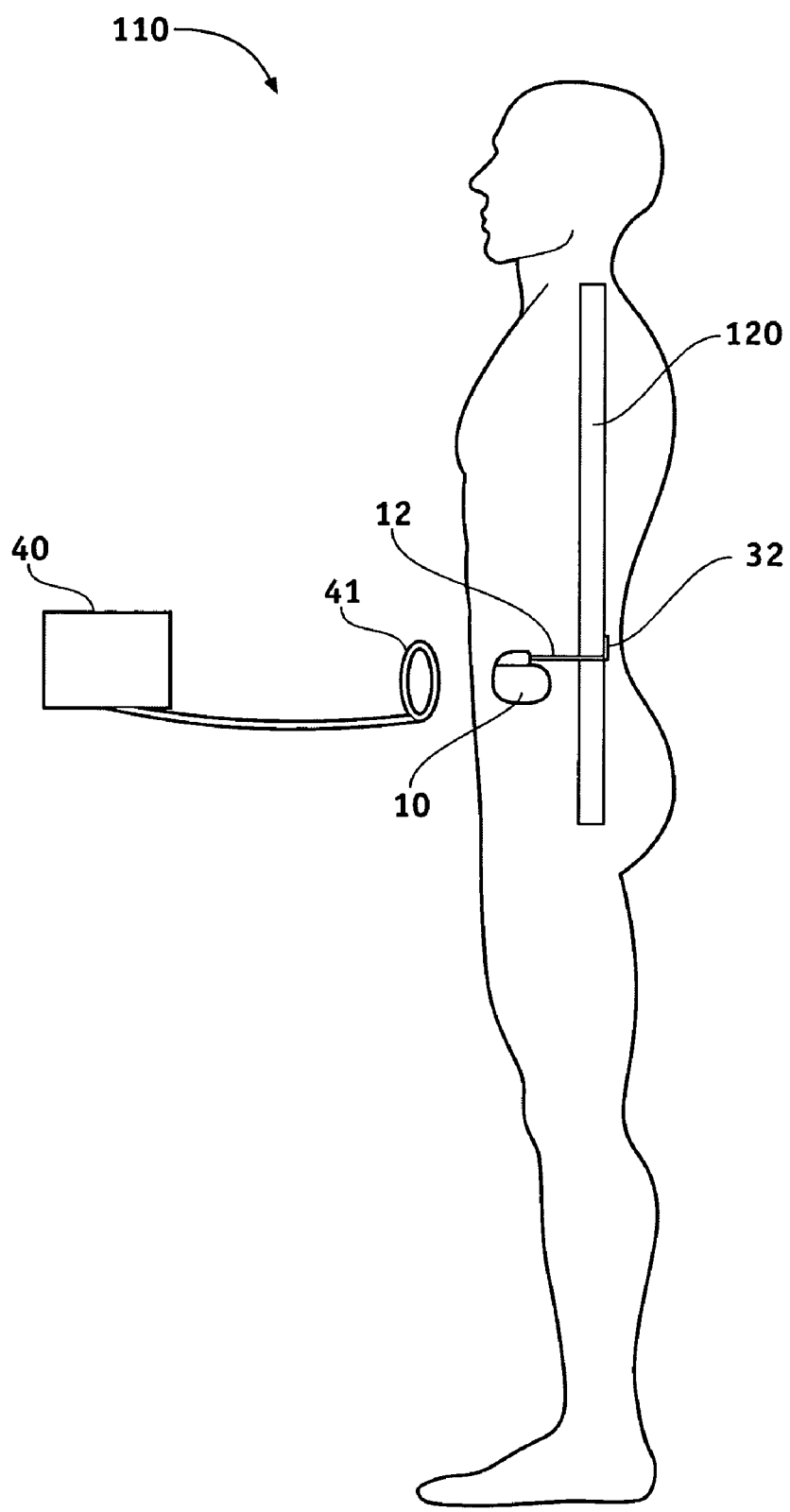
FIG. 2 is an illustration of a patient with an implantable pulse generator implanted in the patient's abdomen and a lead connected to the pulse generator placed in the epidural space next to the spinal cord according to an embodiment of the present invention.

While the following description is generally directed to treatments and systems involving a neurological stimulator in the form of an implantable pulse generator, the utility of the apparatus and method of the present invention is not limited to neurostimulatory pulse generating devices and can be adapted for use with a variety of implantable electrical devices that use multiple electrical leads to send electrical pulses to selected body parts. FIG. 2 is an illustration of a patient 110 with an implantable pulse generator (IPG) 10 implanted in the patient's abdomen. The IPG 10 transmits independent stimulation pulses to the spinal cord 120 using an insulated lead 12 and electrodes 32 coupled thereto. The lead 12 is routed around the flank toward the spinal column 120, and the electrodes 32 are placed in the epidural space next to the spinal column 120. An extension (not shown), including a conductor, may also be used to electrically connect the IPG 10 to the lead 12.

In order to manipulate the location of the electrical field produced by the electrodes 32, the IPG 10 includes a plurality of outlets as necessary to selectively and independently control each electrode 32 to which the IPG 10 is coupled. According to one exemplary embodiment, the IPG 10 includes sixteen channels and respective outlets to control a field steerable stimulation lead including sixteen electrodes. In an alternative exemplary embodiment, the IPG 10 has fewer independent channels and respective outlets than the number of leads controlled thereby, and transmits coded address signals before each stimulation pulse to instruct which of the electrodes will transmit pulses to a patient. Electronics are disposed downstream from the IPG 10 on the lead to receive the coded address signals and, responsive thereto, to select and control the electrodes indicated by the coded signals.

The IPG 10 and the associated system typically utilize fully implantable elements, although it is within the scope of the invention to utilize partially implanted generators that employ wireless coupling technology such as electronic components sold by Medtronic, Inc. under the trademarks X-trel™ and Mattrix™. A wireless receiver in the IPG 10 can be adapted to receive instruction commands from a physician or another user, the instruction commands selecting stored pulse output commands from the IPG 10 or programming new pulse output commands. Also, according to either of the exemplary embodiments described above, the IPG 10 includes a memory for storing pulse output commands that can be programmed in advance of implantation and are tailored to a patient's needs. The output commands can be transmitted directly to the selected electrodes. In another embodiment, the output commands are encoded in address signals that are transmitted to a downstream electronic network that decodes and generates pulse output commands and transmits them to selected electrodes. The electrodes can be programmed individually, or controlling programs can generate commands that are transmitted to predetermined groups of electrodes depending on the patient's needs.

After the IPG 10 is implanted, the pre-programmed pulse output commands can be modified using an external programmer 40 that communicates wirelessly with the IPG 10. The programmer 40 is equipped with an antenna 41 for wireless communication, and the IPG 10 is equipped with a receiver (not shown). The programmer 40 can communicate using any suitable known communication signals including but not limited to radio frequency signals. Wireless communication with the IPG 10 enables a physician or the patient to non-invasively relocate the electrical field after the IPG 10 is implanted, and to thereby adjust the dorsal column stimulation. Because specific fibers on the dorsal column can be electrically stimulated or not stimulated through post-surgical manipulation, the intricacy of implanting the IPG leads and electrodes 32 is substantially reduced. The physician performing the surgery can implant a lead body that houses the IPG electrodes 32 in a general area on the dorsal column and then later steer or alter the electrical field using the programmer 40.

In a general sense, manipulating and adjusting the excitation locus can be performed using known techniques. Although the present invention is directed to fine tuning tissue stimulation, general techniques such as those described in U.S. Pat. No. 5,713,922, incorporated herein by reference, for neural tissue excitation adjustment in the spinal cord or brain can be used in combination with the present invention.

Figure 3:
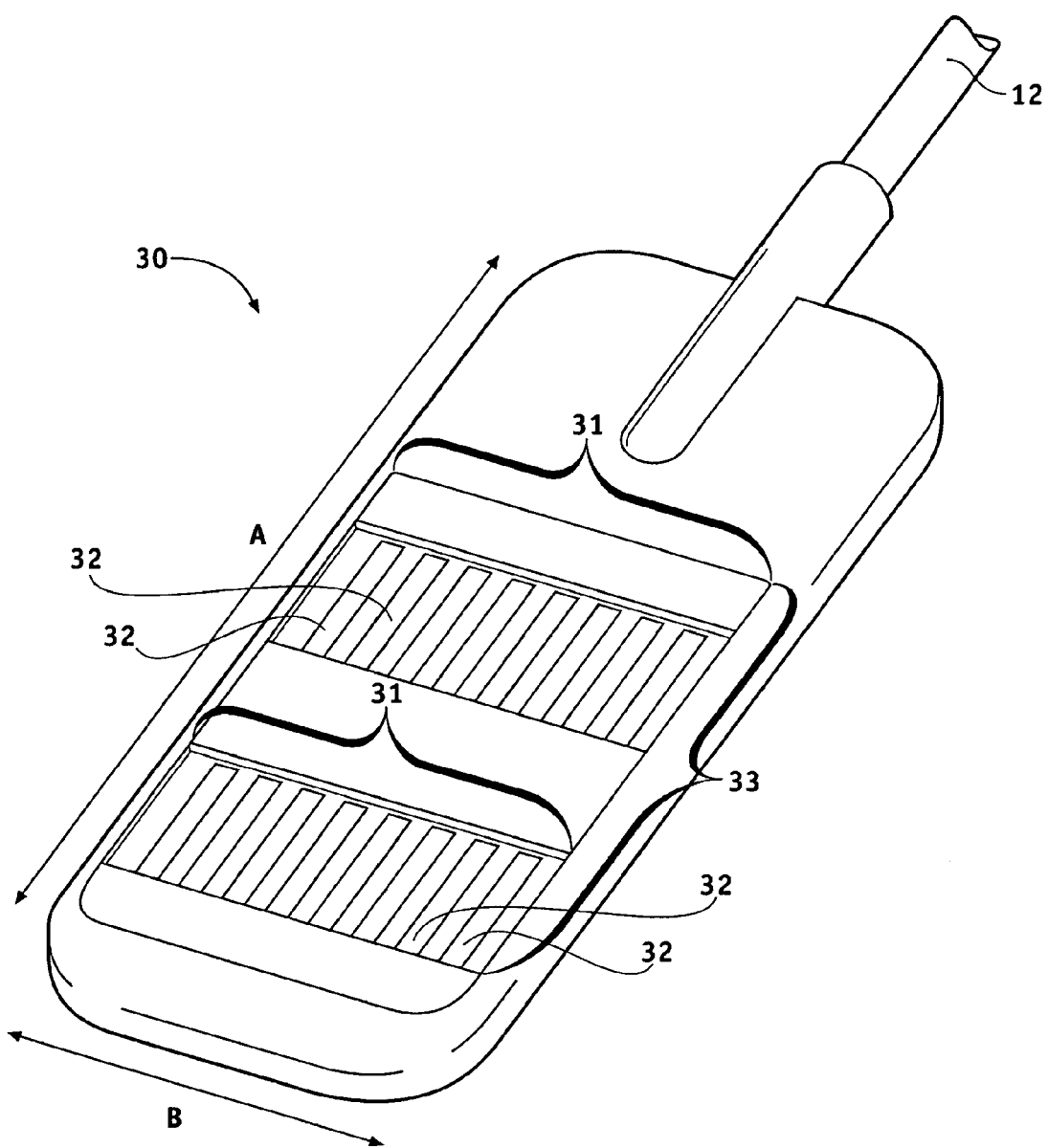
FIG. 3 is a top view of an exemplary electrode paddle 30 according to an embodiment of the present invention.

Steering or altering the IPG electrical field is further enabled according to the present invention by a fine tuning apparatus that secures and distributes the stimulating electrodes in the dorsal column vicinity. FIG. 3 is a top view of an exemplary electrode paddle 30. The electrode paddle 30 provides a hermetic encasement for circuitry and electronics, and also secures and supports many small and closely spaced electrodes 32. The electrode paddle 30 and the electrodes 32 exposed thereon are formed using biostable materials, and the electrodes 32 are secured in the housing in a manner whereby corrosive body fluids are unable to contaminate the paddle interior and corrode or otherwise disrupt the electrode circuitry 32. The electrode paddle 30 organizes the electrodes 32 into one or more groups 31, and in an exemplary embodiment the electrodes 32 are organized into at least two groups 31. The intra-group and inter-group electrode distribution on the electrode paddle 30 prevents the electrodes from contacting one another, and at the same time creates a dense electrode region 33. The dense electrode region 33 permits the electrode paddle 30 to be small despite the large number of electrodes 32 secured thereon, and therefore to be positionable in the dorsal column vicinity with minimal impact on body tissues.

The exemplary electrode paddle 30 in FIG. 3 includes two electrode groups 31, with eight electrodes 32 in each group 31. The groups 31 are spaced apart in the longitudinal direction A of the electrode paddle 30, and the electrodes 32 within each group 30 are spaced apart in the lateral direction B. Although the number of electrodes and their precise configuration on the electrode paddle 30 can vary without varying from the scope of the present invention, the configuration illustrated in FIG. 3 provides closely-spaced electrodes 32 that can be individually controlled to steer the electrical field that is therapeutically provided to a patient. In an exemplary embodiment the electrodes are each about 0.5 mm wide and are consistently spaced about 0.5 mm apart, although other electrode sizes and spacing may be suitable. For example, the electrodes can be spaced between about 0.1 mm and about 10 mm apart, and are preferably spaced between about 0.1 mm and about 0.5 mm apart.

When two electrodes are spaced about 0.5 mm apart, switching the electrical pulses from one electrode to the nearest laterally adjacent electrode laterally shifts the electrical field center about 0.5 mm. For an even more precise shift and a higher current, both of the two adjacent electrodes can be selected, causing the electrical field to be centered between the two electrodes and to have a larger current. Also, in some cases a high current may required to effectively stimulate a desired nerve fiber, and the voltage capability of the IPG 10 may be exceeded. The electrodes 32 are so closely spaced on the electrode paddle 30 that two or more electrodes 32 may be selected simultaneously to effectively function as a single larger electrode. With the electrode paddle 30 implanted in the dorsal column vicinity, selected nerve fibers can be carefully and precisely stimulated by steering the electrical field between the electrodes 32 in this manner.

The electrode paddle 30 can be used in combination with other known voltage divider systems as appropriate. U.S. Pat. Nos. 5,501,703 and 5,643,330, and Publication WO 95/19804, are incorporated herein in by reference. These references disclose, inter alia, an electric field steering process that involves individually controlling the voltage at each of a plurality of electrodes. More particularly, the references disclose individually manipulating the voltage of at least three electrodes that are incorporated in a multichannel apparatus for epidural spinal cord stimulation.

Figure 4:
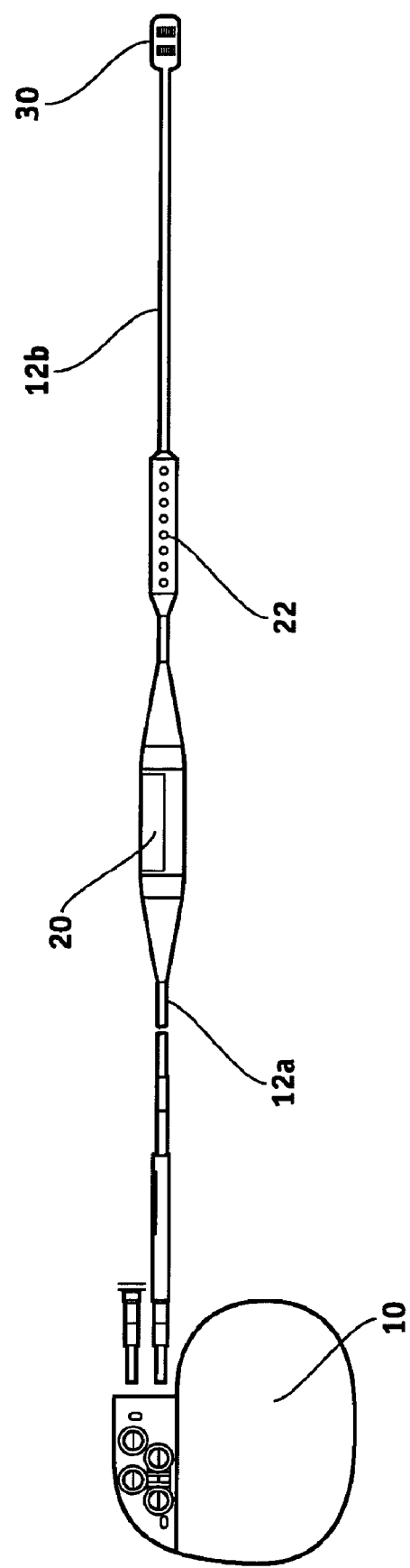
FIG. 4 is a top view of a medical device assembly including an implantable pulse generator, a first lead body portion, an in-line hermetic encasement, and a second lead body portion that are electrically connected in sequence according to an embodiment of the present invention.

In an exemplary embodiment of the invention, electronics are provided on the lead between the electrode paddle 30 and the IPG 10. A coded signal is sent from the IPG 10 to an electronics package that selectively activates the electrodes 32 in response. FIG. 4 is a top view of a medical device assembly including the IPG 10, a first lead body portion 12a, an in-line hermetic encasement 20, and a second lead body portion 12b that are electrically connected in sequence. Each lead body 12a, 12b may include one or more leads that may be combined in one or more lead bodies. When the assembly is implanted, the first lead body portion 12a is electrically coupled to the IPG 10, and extends to another suitable location in the patient's body where it is electrically coupled to a hermetic electronic encasement 20. The encasement 20 houses an electronic network that may include a memory for storing programs that, when carried out, enable the electronic network to communicate with and control multiple electrodes disposed on the electrode paddle 30. The encasement 20 may further include at least one energy source such as a battery to power the electronic network and the electrode paddle 30. An exemplary embodiment of the encasement 20 and its contents will be described in greater detail below.

A plurality of leads collectively identified as the lead body portion 12b are electrically coupled to the encasement 20 at one end and are directly engaged or indirectly coupled with the electrode paddle 30 at an opposite end. Optionally, a connector block 22 can be fastened to the encasement 20. The connector block 22 electrically connects one or more leads to the encasement 20 via connectors such as lead clamps (not shown) that hold the leads in place.

Figure 5:
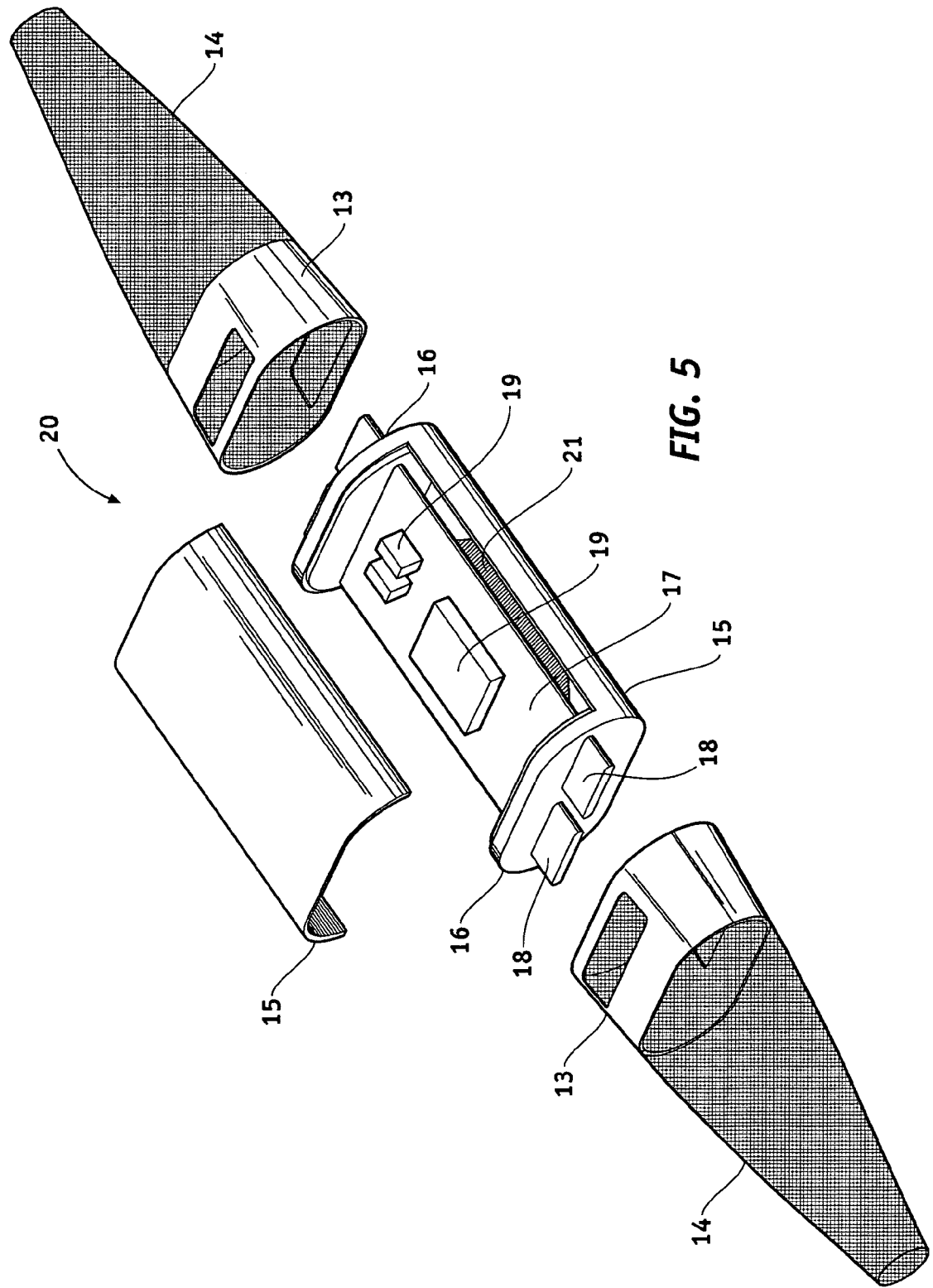
FIG. 5 is an exploded view of the hermetic electronic encasement depicted in FIG. 4.

FIG. 5 is an exploded view of a hermetic electronic encasement 20 disclosed in U.S. patent application Ser. No. 10/742,732 which is incorporated herein by reference. As mentioned above, the encasement 20 serves as the housing for electronic intelligence and other components such as at least one energy source 21, and integrated electrical circuitry/components 19. The encasement 20 is in-line with the lead body 12a, 12b and consequently enables the electrode paddle 30 and, optionally, other stand-alone devices or components that may be controlled by the IPG 10 to be disposed downstream from and in direct communication with the IPG 10.

Although the energy source 21 may be a simple battery, the hermetic encasement 20 may be powered by dedicated conductive lines from the IPG 10. In another embodiment, the energy source 21 harvests or rectifies power from the IPG 10 stimulation pulses and stores the same in order to power the hermetic encasement 20 and the electrode paddle 30. In yet another embodiment, the hermetic encasement 20 is temporarily powered via an external magnetic field or RF energy.

The electrical circuitry/components 19 are integrated into or mounted onto a multi-layered circuit board 17 formed of biostable materials. In an exemplary embodiment of the invention the circuit board 17 is a multi-layered ceramic structure that includes surface bonding pads 18 for coupling the circuitry/components 19 to the lead body 12a, 12b. The bonding pads 18 are deposited onto the circuit board 17 using any conventional depositing method and are formed from a biocompatible metal such as gold or platinum. Examples of depositing techniques include printing, chemical vapor deposition, or physical deposition such as sputtering.

The encasement assembly can include side walls 15 that combine to surround the mid-portion of the circuit board 17, and end walls 16 that are attached to the side walls 15 to complete the encasement 20. In an exemplary embodiment of the invention, the end walls 16 and side walls 15 are composed of a ceramic material. In order to protect and maintain the connections between the bonding pads 18 and the lead body 12a, 12b a flexible strain relief device 14 can be attached to one or both of the encasement ends. An adaptor 13 can be coupled to the strain relief device 14 to appropriately shape the device 14 and provide rigidity to the portion of the device 14 that interfaces with an endplate 16.

In another exemplary embodiment of the invention, an integrated lead system is employed in which electronics are provided on the electrode paddle 30, or on another lead extension in communication with the electrode paddle 30, to allow use of large numbers of electrodes with a small number of conductors extending along the lead wire and/or extension. A coded signal is provided to the electrode paddle 30 from the IPG, and the electrode paddle electronics identify which electrodes to activate in response thereto. More particularly, the electronics on the electrode paddle 30 include a controller that responds to the coded signal and selectively activates the electrodes 32. The electronics may be included within the paddle housing or may be separately housed adjacent to the electrode paddle 30. The embodiments described above or within the scope of the invention as described herein can be used in combination with additional known electronics for selecting and controlling electrode arrays. See, for example, U.S. Pat. No. 6,038,480 (Hrdlicka et al) on living tissue stimulation and recording techniques with local control of active sites; U.S. Pat. No. 6,473,653 (Schallhom et al) on selective activation of electrodes within an implantable lead, and US Patent Application Publication No. US2003/0093130A and PCT Patent Publication No. WO2003/041795A (Stypulkowski) on multiplexed electrode array extensions, all three of which are incorporated herein by reference in their entirety.

Figure 6:
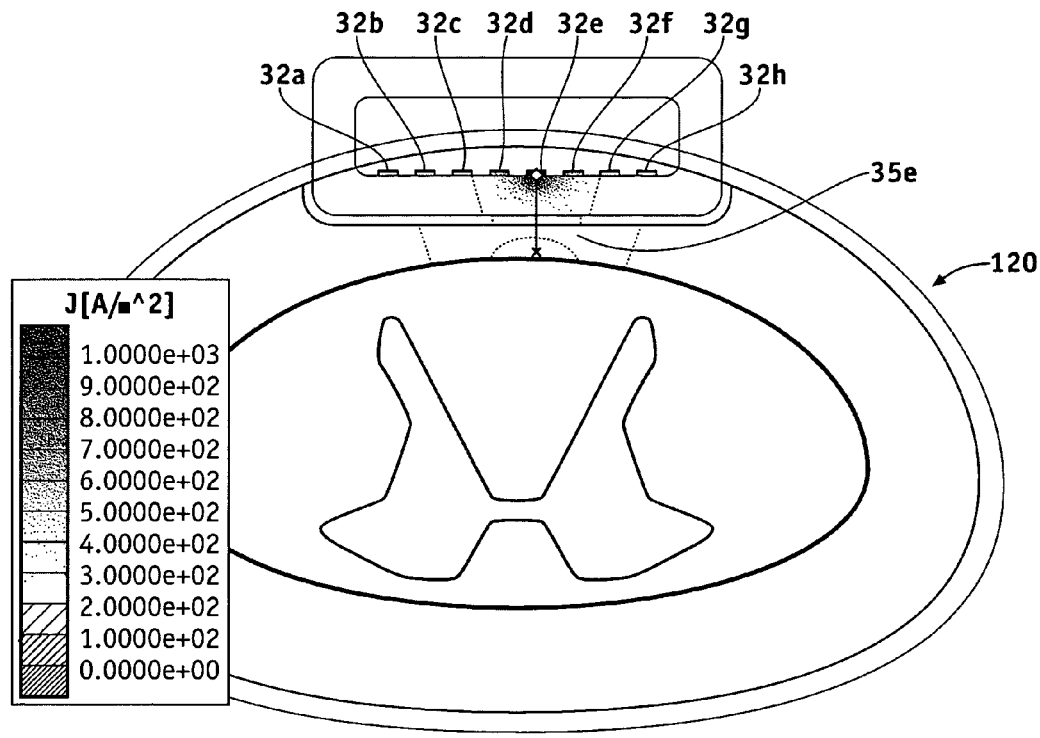
FIGS. 6 to 9 are images from a computer model of electrical fields, illustrating the effect of selecting different electrodes to supply stimulation to the spinal cord according to an embodiment of the present invention.
Figure 7:
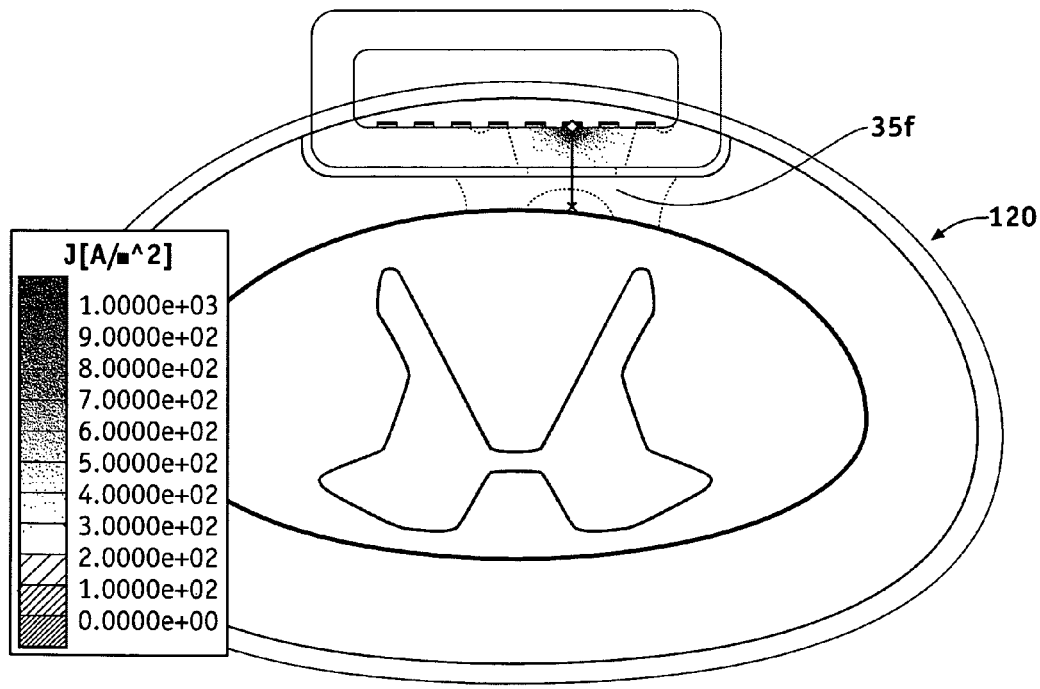
Figure 8:
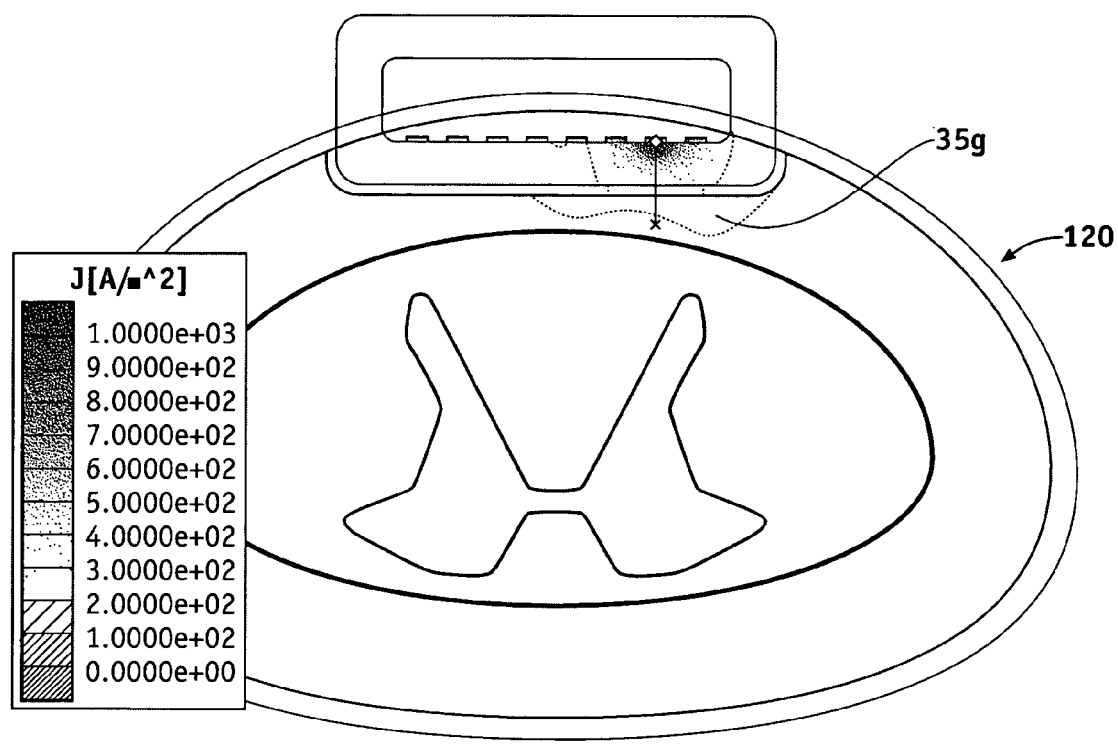
Figure 9:
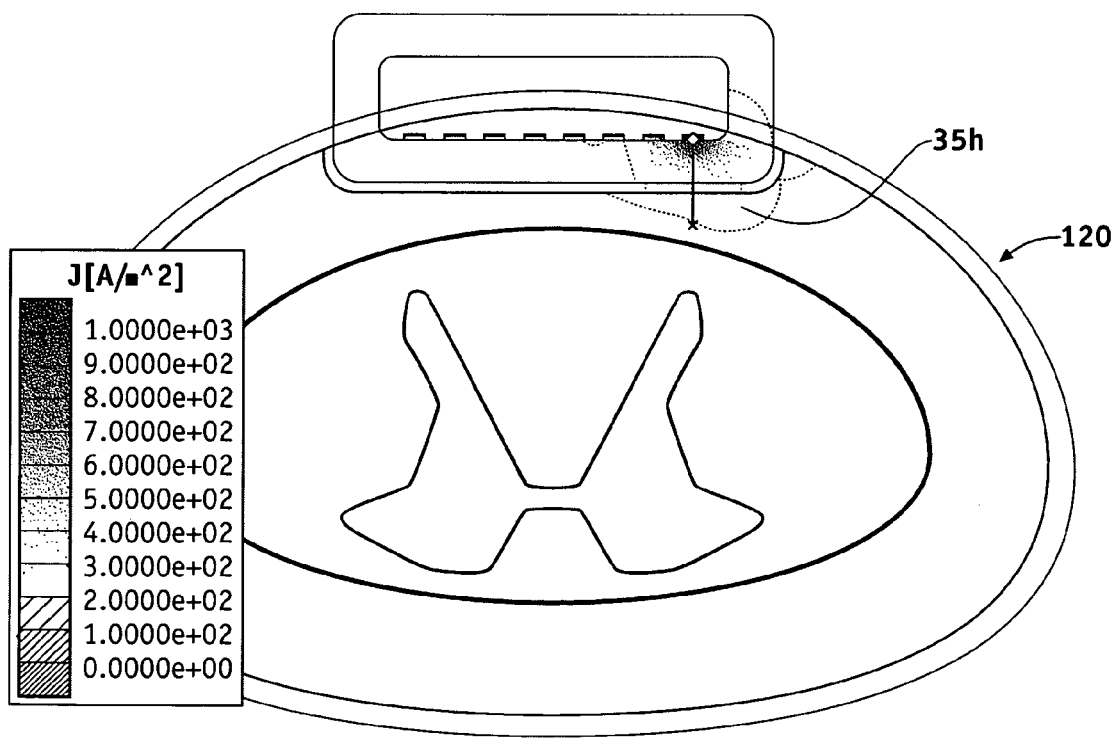

Returning now to the functional aspects of the invention, FIGS. 6 to 9 are images from a computer model of electrical fields, illustrating the effect of selecting different electrodes to supply stimulation to the spinal cord. More particularly, the figures illustrate the result of a computer modeling study of the electrical field generated by an electrode. Each figure is a cross section of the spinal cord 120, with an eight-electrode paddle 30 located in the epidural space. The eight electrodes 32 are designated as electrodes 32a, 32b, 32c, 32d, 32e, 32f, 32g, and 32h progressing upwardly from left to right with electrode 32a on the far left. The electrode-generated electrical field is steerable about the spinal cord 120 as different electrodes 32 are selected. In the figures, the electrodes 32 are spaced 0.5 mm apart, although such spacing is merely exemplary and can be adjusted depending on the patient's needs. In FIG. 6, electrode 32e is selected, generating an electrical field 35e about a spinal cord area. In FIG. 7, electrode 32f is selected and the electrical field 35f changes its shape and position to stimulate a different spinal cord area. The fields 35g, 35h are shown in FIGS. 8 to 9, respectively, as electrodes 32g and 32h are selected.

Figure 10:
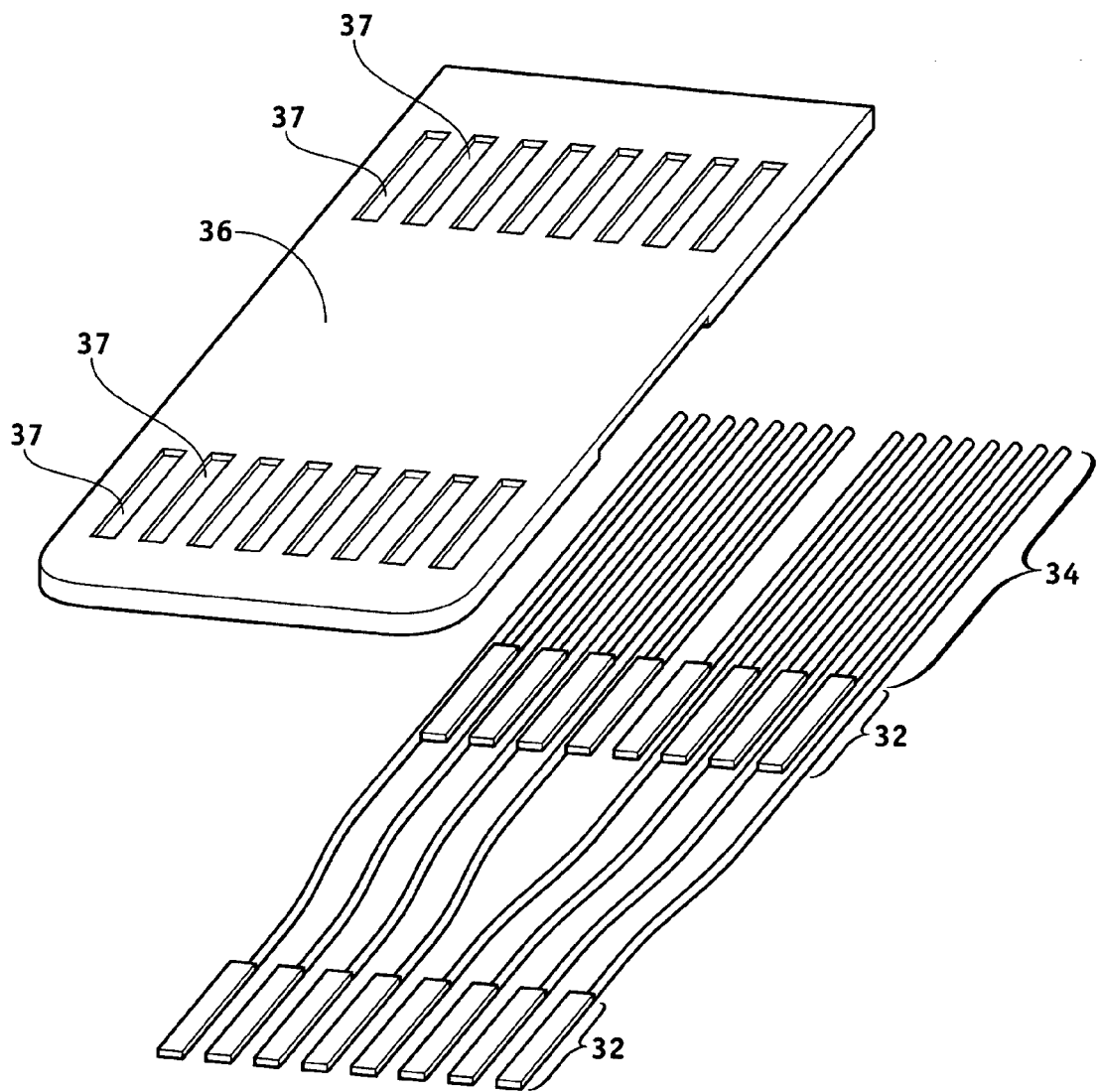
FIG. 10 is an exploded view of a substrate and wire-electrode assemblies to be mounted thereon to manufacture an electrode paddle according to an embodiment of the present invention.

Exemplary methods for manufacturing the electrode paddle 30 will now be discussed. FIG. 10 is an exploded view of a substrate 36 and wire-electrode assemblies to be mounted thereon. The individual electrodes 32 are formed from any suitable conductive metal such as platinum-iridium. The wire-electrode subassemblies are then individually assembled onto a substrate 36 that includes a window 37 for each electrode 32 that exposes the electrode 32 to the spinal cord. The substrate 36 is typically polyurethane, but can be formed from a fiberglass, a polyimide, a thermoset elastomer such as silicone, another suitable polymer such as an injection molded polymer, or another suitable nonconductive material. The wire-electrode subassemblies are assembled onto the substrate 36 by a suitable technique. Alternatively, the electrodes 32 may be directly deposited onto the substrate 36 using a deposition process, or an etching process using a completely metallized surface as a starting material. One of the above processes is typically performed to first deposit or otherwise assemble the electrodes 32, and thereafter form the wires 34 and join them to the electrodes 32 using a laser welding method, a crimping method, or other suitable joining process. Although not shown in FIG. 10, an insulative backing substrate may be adhered or otherwise joined to or be integral with the substrate 36 to shield and further isolate the electrodes 32 and wires 34 from the external environment and from each other.

Figure 11:
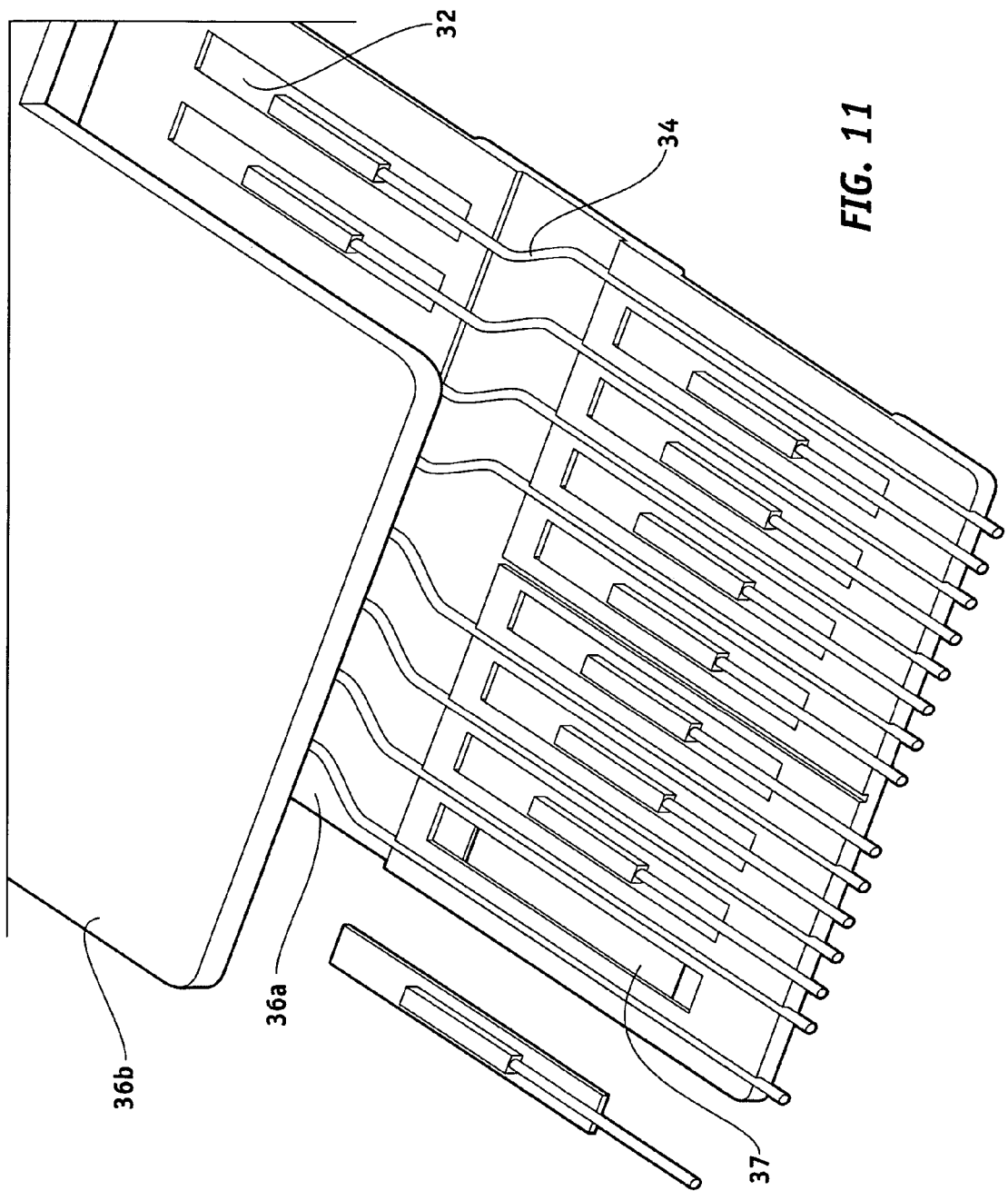
FIG. 11 is an exploded view of substrate sheets securing electrodes and routing wires to manufacture an electrode paddle according to an embodiment of the present invention.

In an exemplary embodiment, the substrate 36 includes two sheets 36a, 36b. FIG. 11 is an exploded view of the substrate sheets 36a, 36b securing the electrodes 32 and routing the wires 34. The sheets 36a, 36b are made from a resin such as polyurethane, or another suitable material as recited above. The electrode/wire assemblies are coupled using a process selected from those processes recited above, and are placed in slots 37 in sheet 36a. The electrodes 32 may be temporarily retained using adhesive or a heated probe to melt small amounts of polyurethane over each electrode 32. The other polyurethane sheet 36b is then placed on top of the first sheet 36a and the electrode/wire assemblies, trapping the wires and electrodes. Adhesive or heat staking may be used to temporarily retain the electrodes 32 and wires 24 for handling. The entire assembly 36 is then placed in a hot fixture, and a hot plate presses the sheets 36a, 36b. The heat allows the softened polyurethane to flow about any open spaces to encapsulate the electrode/wire assemblies and seal the sheets together with a fluid-impermeable seal.

Figure 12:
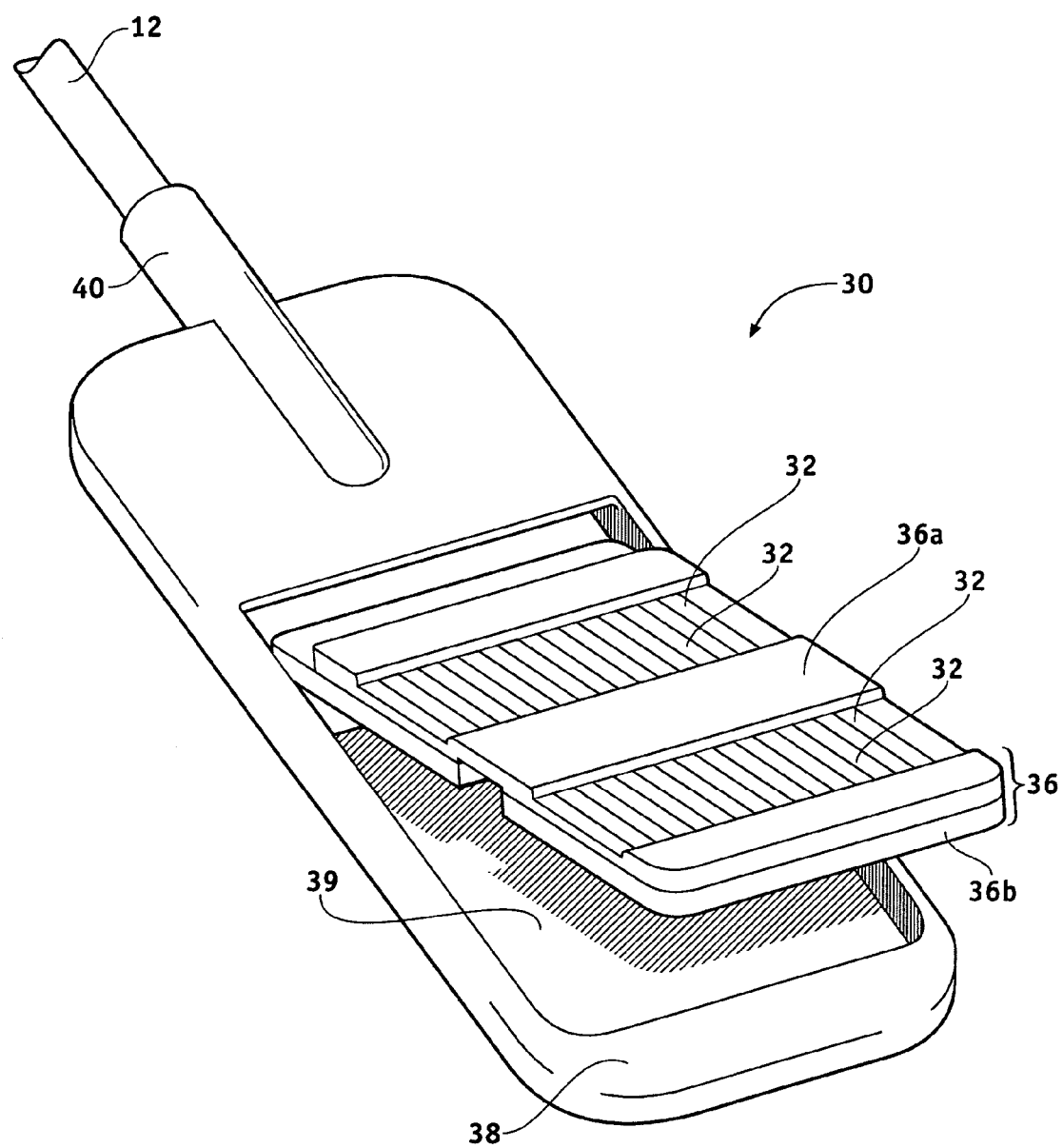
FIG. 12 is an isometric view of the substrate sheets depicted in FIG. 11 being fit into a boot to manufacture an electrode paddle according to an embodiment of the present invention.

FIG. 12 is an isometric view of the substrate 36 being fit into a boot 38. The boot 38 is made of silicone, polyurethane, or other suitable nonconductive material, and includes a receiving slot 39 in which the substrate 36 is received and then slidingly engaged. The slot 39 is of a depth that causes the top surface of sheet 36a to be flush with the top surface of the boot 38, and is sized to expose the electrodes 32 to the spinal cord to the boot exterior. Thus, the paddle 30 can be implanted with the electrodes 32 uniformly distanced from the spinal cord. After the substrate 36 is secured in the boot 38, the wires 34 are routed into a connection tube 40 and joined to one or more lead bodies 12. Adhesives such as silicone RTV or other sealants may be used to fill in any holes or to secure any panels that were installed during the manufacturing process.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An implantable electrode paddle adapted to receive an electrical signal from a medical device and generate an electrical field to stimulate selected body tissue, the electrode paddle comprising:
    a housing including walls that define an interior space and a plurality of windows formed through at least a first one of the walls for transmitting the electrical field to the body tissue, the housing having a longitudinal dimension that is greater than a lateral dimension of the housing;
    an electrode array including a plurality of longitudinally spaced electrode groups with each separated by a portion of the walls of the housing with longitudinal spacing of the electrode groups being in a direction of the longitudinal dimension of the housing, each electrode group including at least two electrodes that are individually secured in a respective window, that are immediately laterally adjacent, and that are laterally spaced from closest edge to closest edge by an amount that is less than the longitudinal spacing from closest edge to closest edge between the electrode groups that are immediately longitudinally adjacent, where the lateral spacing between the immediately laterally adjacent electrodes from closest edge to closest edge is between about 0.1 mm and less than 1 mm, and where the lateral spacing from closest edge to closest edge between two immediately adjacent electrodes of a first electrode group of the plurality is the same as the lateral spacing from closest edge to closest edge between two immediately adjacent electrodes of a second electrode group of the plurality that is longitudinally spaced from the first electrode group, with at least one electrode of at least one electrode group having an applied common electrical potential relative to an immediately laterally adjacent electrode of the at least one electrode group; and
    a plurality of wires, each of the wires being coupled to a respective electrode and routed within the interior space to receive the electrical signal.

2. The implantable electrode paddle according to claim 1, wherein the immediately laterally adjacent electrodes in each electrode group are laterally spaced apart from closest edge to closest edge by 0.5 mm.

3. The implantable electrode paddle according to claim 2, wherein there are two electrode groups, each group consisting of eight electrodes.

4. The implantable electrode paddle according to claim 1, further comprising:

an electronic network housed within the interior space and adapted to receive the electrical signal and, in response thereto, to select and transmit electrical pulses to one or more of the electrodes.

5. The implantable electrode paddle according to claim 1, wherein the electrodes within each group are evenly spaced apart.

6. An implantable lead system adapted to transmit an electrical signal from a medical device and generate an electrical field to stimulate selected body tissue, the system comprising:
   a first lead body comprising at least one conductor; and
   an electrode paddle, comprising:
   a housing including walls that define an interior space and a plurality of windows formed through at least a first one of the walls for transmitting the electrical field to the body tissue, the housing having a longitudinal dimension that is greater than a lateral dimension of the housing;
   an electrode array including a plurality of longitudinally spaced electrode groups with longitudinal spacing of the electrode groups being in a direction of the longitudinal dimension of the housing, each electrode group including at least two electrodes individually that are secured in a respective window, that are immediately laterally adjacent, and that are laterally spaced from closest edge to closest edge by an amount that is less than the longitudinal spacing from closest edge to closest edge between the electrode groups that are immediately longitudinally adjacent, where the lateral spacing between the immediately laterally adjacent electrodes from closest edge to closest edge is between about 0.1 mm and less than 1 mm, and where the lateral spacing from closest edge to closest edge between two immediately adjacent electrodes of a first electrode group of the plurality is the same as the lateral spacing from closest edge to closest edge between two immediately adjacent electrodes of a second electrode group of the plurality that is longitudinally spaced from the first electrode group, with at least one electrode of any one of the electrode groups having an applied common electrical potential relative to an immediately laterally adjacent electrode of the electrode group; and
   a plurality of wires, each of the wires being routed within the interior space and coupled to a respective electrode and to the first lead body.

7. The implantable lead system according to claim 6, further comprising:
   a hermetic encasement, comprising:
   a housing defining an interior space,
   an electronic network housed within the interior space,
   a first set of one or more terminals electrically coupling the electronic network to the electrode paddle, and
   a second set of one or more terminals electrically coupling the electronic network to the first lead body.

8. The implantable lead system according to claim 7, further comprising:
   a second lead body comprising at least one conductor having a first end that is electrically coupled to at least one of the terminals in the first set, and a second end that is electrically coupled to the electrode paddle.

9. The implantable lead system according to claim 6, wherein the immediately laterally adjacent electrodes in each electrode group are laterally spaced from closest edge to closest edge by 0.5 mm.

10. The implantable lead system according to claim 9, wherein there are two electrode groups, each group consisting of eight electrodes.

11. The implantable lead system according to claim 6, further comprising:
   an electronic network housed within the interior space and adapted to receive the electrical signal and, in response thereto, to select and transmit electrical pulses to one or more of the electrodes.

12. The implantable lead system according to claim 6, wherein the electrodes within each group are evenly spaced apart.

13. An implantable medical device assembly for generating an electrical field to stimulate selected body tissue, the device comprising:
   a controlling device having an electrical output for transmitting electrical signals;
   a first lead body comprising one or more electrical conductors, the first lead body having a first end and a second end, the first end being coupled to the electrical output; and
   an electrode paddle, comprising:
   a housing including walls that define an interior space and a plurality of windows formed through at least a first one of the walls for transmitting the electrical field to the body tissue, the housing having a longitudinal dimension that is greater than a lateral dimension of the housing;
   an electrode array including a plurality of longitudinally spaced electrode groups separated by a portion of the walls of the housing with longitudinal spacing of the electrode groups being in a direction of the longitudinal dimension of the housing, each electrode group including at least two electrodes that are individually secured in a respective window, that are immediately laterally adjacent, and that are laterally spaced from closest edge to closest edge by an amount that is less than the longitudinal spacing from closest edge to closest edge between the electrode groups that are immediately longitudinally adjacent, where the lateral spacing between the immediately adjacent electrodes from closest edge to closest edge is between about 0.1 mm and less than 1 mm, and where the lateral spacing from closest edge to closest edge between two immediately adjacent electrodes of a first electrode group of the plurality is the same as the lateral spacing from closest edge to closest edge between two immediately adjacent electrodes of a second electrode group of the plurality that is longitudinally spaced from the first electrode group, with at least one electrode of at least one electrode group having an applied common electrical potential relative to an immediately laterally adjacent electrode of the at least one electrode group; and
   a plurality of wires, each of the wires being routed within the interior space and coupled to a respective electrode and to the first lead body second end.

14. The assembly according to claim 13, wherein the controlling device is an electrical pulse generator.

15. The assembly according to claim 14, wherein the electrical pulse generator includes sixteen channels and sixteen electrical outputs.

16. The assembly according to claim 13, wherein the controlling device comprises:
   a receiver for wirelessly receiving external instruction signals; and
   a processor coupled to the receiver and adapted to produce the electrical signals in response to the instruction signals.

17. The assembly according to claim 16, wherein the electrical signals are pulse output commands, and the controlling device further comprises:
a memory that stores the pulse output commands.

18. The assembly according to claim 13, further comprising:
a hermetic encasement, comprising:
a housing defining an interior space,
an electronic network housed within the interior space,
a first set of one or more terminals electrically coupling the electronic network to the electrode paddle, and
a second set of one or more terminals electrically coupling the electronic network to the first lead body.

19. The assembly according to claim 18, further comprising:
a second lead body comprising at least one conductor having a first end that is electrically coupled to at least one of the terminals in the first set, and a second end that is electrically coupled to the electrode paddle.

20. The assembly according to claim 13, wherein the immediately laterally adjacent electrodes in each electrode group are laterally spaced from closest edge to closest edge by 0.5 mm.

21. The assembly according to claim 20, wherein there are two electrode groups, each group consisting of eight electrodes.

22. The assembly according to claim 13, further comprising:
an electronic network housed within the interior space and adapted to receive the electrical signal and, in response thereto, to select and transmit electrical pulses to one or more of the electrodes.

23. The assembly according to claim 13, wherein the electrodes within each group are evenly spaced apart.

24. An implantable electrode paddle adapted to receive an electrical signal from a medical device and generate an electrical field to stimulate selected body tissue, the electrode paddle comprising:
a housing including walls that define an interior space and a plurality of windows formed through at least a first one of the walls for transmitting the electrical field to the body tissue;
an electrode array including a plurality of longitudinally spaced electrode groups with each separated by a portion of the walls of the housing, each electrode group including at least two electrodes that are individually secured in a respective window, that are immediately laterally adjacent, and that are laterally spaced from closest edge to closest edge by an amount that is less than the longitudinal spacing from closest edge to closest edge between the electrode groups that are immediately longitudinally adjacent, where the lateral spacing between the immediately laterally adjacent electrodes from closest edge to closest edge is between about 0.1 mm and less than 1 mm, and where the lateral spacing from closest edge to closest edge between two immediately adjacent electrodes of a first electrode group of the plurality is the same as the lateral spacing from closest edge to closest edge between two immediately adjacent electrodes of a second electrode group of the plurality that is longitudinally spaced from the first electrode group, with at least one electrode of at least one electrode group having an applied common electrical potential relative to an immediately laterally adjacent electrode of the at least one electrode group, with at least one of the electrode groups including only a single laterally spaced row of the at least two electrodes; and
a plurality of wires, each of the wires being coupled to a respective electrode and routed within the interior space to receive the electrical signal.

25. An implantable electrode paddle adapted to receive an electrical signal from a medical device and generate an electrical field to stimulate selected body tissue, the electrode paddle comprising:
a housing including walls that define an interior space and a plurality of windows formed through at least a first one of the walls for transmitting the electrical field to the body tissue;
an electrode array including a plurality of longitudinally spaced electrode groups with each separated by a portion of the walls of the housing, each electrode group including at least two electrodes that are individually secured in a respective window, that are immediately laterally adjacent, and that are laterally spaced from closest edge to closest edge by an amount that is less than the longitudinal spacing from closest edge to closest edge between the electrode groups that are immediately longitudinally adjacent, where the lateral spacing between the immediately laterally adjacent electrodes from closest edge to closest edge is between about 0.1 mm and less than 1 mm, and where the lateral spacing from closest edge to closest edge between two immediately adjacent electrodes of a first electrode group of the plurality is the same as the lateral spacing from closest edge to closest edge between two immediately adjacent electrodes of a second electrode group of the plurality that is longitudinally spaced from the first electrode group, with at least one electrode of at least one electrode group having an applied common electrical potential relative to an immediately laterally adjacent electrode of the at least one electrode group, with at least one electrode group including at least one electrode that has a longitudinal dimension that is at least three times as large as a lateral dimension; and
a plurality of wires, each of the wires being coupled to a respective electrode and routed within the interior space to receive the electrical signal.

* * * * *